United States Patent [19]

Devos et al.

[11] 4,423,086

[45] Dec. 27, 1983

[54] PROCESS FOR HARD COATING WITH SORBITOL AND PRODUCTS OBTAINED THEREBY

[75] Inventors: Francis Devos, Morbecque-Merville; Guy Bussiere, La Gorgue; Michel Huchette, Merville, all of France

[73] Assignee: Roquette Freres, Lestrem, France

[21] Appl. No.: 276,361

[22] PCT Filed: Oct. 16, 1980

[86] PCT No.: PCT/FR80/00151

§ 371 Date: Jun. 16, 1981

§ 102(e) Date: Jun. 16, 1981

[87] PCT Pub. No.: WO81/01100

PCT Pub. Date: Apr. 30, 1981

[30] Foreign Application Priority Data

Oct. 17, 1979 [FR] France .................................. 79 25840
Apr. 3, 1980 [CH] Switzerland ........................ 2652/80

[51] Int. Cl.³ .............................................. G01K 9/32
[52] U.S. Cl. ........................................ 427/3; 426/548; 424/31

[58] Field of Search ............... 424/31; 427/3; 426/548

[56] References Cited

U.S. PATENT DOCUMENTS

| | | | |
|---|---|---|---|
| 3,185,626 | 5/1965 | Baker | 427/3 |
| 3,480,468 | 11/1969 | Carletti | 427/3 |
| 4,127,645 | 11/1978 | Witgel | 426/548 |
| 4,241,092 | 12/1980 | Halik | 426/548 |
| 4,293,570 | 10/1981 | Vadaoz | 426/548 |

FOREIGN PATENT DOCUMENTS 1264451  2/1972  United Kingdom ................... 427/3

*Primary Examiner*—Sam Silverberg
*Attorney, Agent, or Firm*—Larson and Taylor

[57] ABSTRACT

Process for hard coating with sorbitol. On the one hand, a sorbitol syrup having a concentration of 60 to 85% by weight is supplied on a moving bed of cores to be coated and, on the other hand, the temperature prevailing in the bed is kept at a value comprised between 50° and 10° C. The present coating process applies conveniently to cores of the "without sugar" type in the field of confectionery and pharmaceutical products.

22 Claims, No Drawings

PROCESS FOR HARD COATING WITH SORBITOL AND PRODUCTS OBTAINED THEREBY

The invention relates to a method for hard coating (preparing hard dragees).

It also relates to, as novel industrial products, the coated products so obtained.

It will be recalled that, by the expression "hard coating" is meant any process consisting of coating a preformed element or core with an adherent envelope,
- protecting the core against external physicochemical agents including atmospheric moisture and the oxygen of the air,
- conferring on the finished article a greater mechanical strength against shock and abrasion as well as a more attractive appearance and a particular flavor or taste.

The concept of so-called "hard" coating is distinguished from that of so-called "gentle" (soft) in that it implies complete crystallization of the envelope with the evaporation of all the water contained in the constituent material of the latter.

It is in the confectionary industry and pharmaceutical products that hard coating finds its principal uses, it being recalled that "confectionery" which can be coated comprises notably chewing-gums, chewing pastes, sweets (candies) and liquorice, and that pharmaceutical products, liable to be coated, are constituted notably by tablets, pills or bonbons including medicinal substances or active principles.

Both confectionery and the above-mentioned pharmaceutical products may be of the conventional type, that is to say, including sugars such as saccharose, dextrose, fructose or glucose syrups; they may also be of the "sugarless" ("without sugar") type, that is to say based notably on polyols such as sorbitol, xylitol, mannitol or the non-cariogenic hydrogenated hydrolysate known under the trade-mark LYCASIN ®, and devoid of saccharose, dextrose, fructose, glucose syrups or equivalent products.

The coating of the core is carried out in a tilted tub rotating around its axis and called a dredger, inside of which there is a plurality of cores forming a moving mass, at the surface of which the constituent material of the future envelope is distributed.

This constituent material is conventionally saccharose.

Now, saccharose, like other sugars such as dextrose or fructose, has undesirable biological effects, notably from the point of view of dental caries. It can in fact very easily and very rapidly become acid because of the bacteria of the mouth. In addition, the sweet flavor of the saccharose is often little liked, especially in the hot season, the consumer then seeking in chewing-gums and confectionery generally, a refreshing and less sweet flavor.

It is, or course, particularly when the core is "sugarless" that the cariogenic character of the saccharose, when the latter is used for the formation of the coating, becomes redhibitory.

It is therefore quite naturally been suggested to resort in this case, to constitute the envelope during the coating process, to polyols already used for the constitution of confectionary or "sugarless" pharmaceutical products intended to be formed into dragees.

It happens that only xylitol and, to a lesser extent, mannitol are at present used for this purpose. They possess in fact, contrary to sorbitol, a hygroscopicity which is not high and good tendency to crystallization, the latter being carried out fairly easily from their aqueous solutions to give crystals of a well-defined type.

To achieve a satisfactory result with xylitol, it has however been necessary to turn to the addition of manufacturing auxiliary substances or additives, such as various fatty materials, various binders or suspending agents, the envelopes with xylitol alone changing rapidly in the course of time and forming small cracks, their outer surface, smooth initially, becoming wrinkled and the internal structure of the envelope, which has initially a microcrystalline character, assuming a rough structure unpleasant to the palate on chewing; in any case, it is no longer possible to speak then of a hard coating with xylitol, similar to that effected with saccharose.

As regards sorbitol, it is reputed to be completely inapplicable in a hard coating process. Thus, it has been clearly indicated, for example, that sorbitol can only be used as an ingredient of the core and not of the envelope, by reason of its hygroscopic nature. It is known, in addition, that the crystallization of sorbitol is much more difficult than that of xylitol and of mannitol and that this difficulty is aggravated by the fact that sorbitol can be obtained in several different crystalline forms only the gamma form constituting a stable form.

A known coating process indeed uses sorbitol as a coating agent, but associated with an excess of xylitol and, on the other hand, the coating syrup is not constituted by a concentrated aqueous solution of sorbitol and xylitol, but by a melted mass of sorbitol and xylitol kept at a temperature between 85° and 90° C. It is known, also, that sorbitol and xylitol cannot be used satisfactorily in coating processes, and that if, for example, sorbitol or xylitol are sprayed onto the cores in the form of an aqueous 50 or 60% solution, as is usual for saccharose solutions, brittle, cracked and irregular products are obtained.

Now, taking into consideration notably the cost price of sorbitol which is distinctly less, relative to the above-mentioned xylitol and mamitol, the Applicant Company, and this despite the above-mentioned definitely unfavorable opinions existing with respect to the use of sorbitol in coating processes, pursued its investigations further and has had the merit of discovering that, unexpected and surprisingly, hard coating with sorbitol was possible provided that a certain number of operational conditions were respected, the dragee products then obtained satisfying the various desiderata of practice.

Consequently, the process of hard coating with sorbitol, according to the invention, is characterized by the fact that:

On the one hand, the sorbitol is applied by the addition, to a moving bed of cores to be coated, of a syrup having a concentration of dry matter comprised between 60 and 85% by weight, preferably between 62 and 80% by weight and, more preferably again, between 65 and 77% by weight, the richness of the syrup in D-sorbitol being greater than 80%, preferably than 95% and, still more preferably, than 99%.

on the other hand, the temperature existing in the moving bed of cores to be coated is kept at a value below 55° C., preferably comprised between 50° and 10° C. and, more preferably again, between 40° and 15° C., all of these conditions being selected, within the indicated limits, so that, when the sorbitol syrup arrives in contact with the cores to be coated, that is to say at the temperature maintained in the moving bed, it finds itself at a saturation level comprised between 0.65 and 1.25, preferably between 0.8 and 1.15.

In one of the advantageous embodiments of the above-said process, the temperature of the sorbitol syrup applied is less than 100° C., preferably than 90° C. and, more preferably again, than 70° C.

It will be recalled that, by the expression "saturation level", is meant the ratio, for a given temperature, of the concentration of the syrup expressed in grams of sorbitol per 100 cm$^3$ of water, to the solubility limit of the sorbitol, at the given temperature, also expressed in grams of sorbitol per 100 cm$^3$ of water; in any event, below are given the values of the solubility limit of the sorbitol for a certain number of temperatures:

| t °C. | Solubility limit (in g/100 cm$^3$) |
|---|---|
| 20 | 220 |
| 25 | 244 |
| 30 | 278 |
| 35 | 317 |
| 40 | 362 |
| 45 | 425 |
| 50 | 500 |

The dragee products according to the invention, notably obtained by means of the above-defined process, are characterised by the fact that the coating is with a sorbitol base, crystalline throughout the thickness of said coating.

The invention will be still better understood with the aid of the additional description which follows and of the examples given with respect to advantageous embodiments.

In order, consequently, to manufacture coated products, procedure is as follows or in equivalent manner.

Into a rotary dredging kettle or tub of conventional type and equipped with internal temperature control means, the cores to be coated of the confectionary or pharmaceutical product type "sugarless" or not, are introduced and there is sprayed onto the moving mass of cores, a sorbitol syrup whose temperature is less than 100° C., preferably than 90° C. and more preferably still than 70° C.

The sprayed sorbitol syrup applied has a concentration of dry matter comprised between 60 and 85% by weight, preferably between 62 and 80% by weight and, more preferably again, between 65 and 77% by weight.

The richness of this syrup in D-sorbitol is greater than 90%, preferably than 95% and, more preferably again than 99%.

The temperature existing in the moving bed of cores is kept at a value below 55° C., preferably comprised between 50° and 10° . C and, more preferably again, between 40° and 15° C.

The concentration of dry matter of the sorbitol syrup, on the one hand, and the temperature of the cores bed, on the other hand, are selected within the above-indicated limits so that, when the sorbitol syrup arrives in contact with the cores to be coated, it is at a saturation level comprised between 0.65 and 1.25, preferably between 0.8 and 1.15.

Conventionally, the coating is done in successive cycles each comprising a first phase of the addition of the sorbitol syrup to the bed of cores and a second phase during which the addition is stopped whilst maintaining the rotation of the tub and the temperature existing in the midst of the mass of cores, the envelope with which the cores have been coated being dried and polished in the course of this phase.

The thickness of the envelope can be selected freely according notably to the core to be coated or the desired effects.

In practice, to produce a coating envelope of 1 mm thickness, 15 to 20 additions should be carried out successively.

The means for maintaining the temperature within the mass of moving cores can be constituted by a controlled temperature hot air blowing device.

By means of the coating conditions according to the invention, at no moment in the process does fusion, nor irregular growth of the sorbital crystals in the course of formation occur, which leads at the end of the operation to a smooth, hard and shiny surface, without "orange peel" phenomena or other surface irregularities.

These conditions moreover maintain a viscosity of the sorbitol syrup such that excellent distribution of the liquid phase on the cores in course of growth is realised and hence rapid crystallization of the sorbitol.

These conditions, associated with the blowing in of hot air, enable the production of very fine crystals and excellent coating.

The Applicant Society has had the considerable merit of observing that it is the conditions mentioned which lead to the desired result; in fact, these conditions are quite contrary to the generally accepted principle, which consists, as for example in the case of saccharose, of operating with high super-saturation to facilitate the formation of the crystals. It happen that, as the Applicant's Company has observed, sorbitol solutions, taken to the same supersaturation conditions as those currently utilized with saccharose (S>1.4) were of too high a viscosity, causing two major drawbacks, namely:

on the one hand, poor distribution of the liquid syrup on the cores, which could result in certain cases in sticking in the kettle, and, on the other hand and especially, considerable delays in crystallization, leading to the formation of incompletely crystallized irregular surfaces and hence having the essential drawbacks of poor stability and the lack of momentary freshness, the latter characteristic constituting an intrinsic property of the stable crystalline form of sorbitol.

It is possible to add to the sorbitol syrup to be sprayed, various additives such as dyes, flavors or agents improving the surface state such as bee wax.

Among the dyes, may be mentioned titanium dioxide, and among the flavorings, those of mint, orange and lemon.

Bonding agents such as vegetable gums and gelatine or fatty substances such as mono- and diglycerides may also be provided. Other sugars such as xylitol or mannitol can also be added to sorbitol.

Among the constituent products of the core to be coated and which can be selected from the group of the confectionary and pharmaceutical products indicated above, particular mention will be made by reason of the non-cariogenic character of the coating obtained according to the invention, of "sugarless" products and, among the latter, of non-cariogenic bonbons based on hydrogenated glucose syrups of the LYCASIN® trademark.

When, on the other hand, the core to be coated contains a fermentable sugar, the coating obtained according to the invention diminishes the cariogenic character of the whole and confers on it in any case the qualities inherent in crystalline sorbitol of the stable type, notably the sensation of freshness.

The invention therefore has a general scope embracing all pharmaceutical products and confectionery to be coated.

From a general point of view, it is emphasized that the coated products according to the invention have a smooth and shiny surface, essentially free of imperfections and crystalline throughout the thickness of the envelope, that they are stable, even in very moist atmospheres and that they have in addition, a very pleasant cool sensation at the moment of consumption, due to the high heat of solution of the sorbitol as well as its high solubility at 37° C.

A. COATING OF A "SUGARLESS" TYPE CHEWING-GUM

"Sugarless" type chewing-gums are prepared according to the method and composition described in French Pat. No. 79-15479 of June 15, 1979.

The composition taken was the following:

| | |
|---|---|
| Base gum type PA-LOJA | 25 parts by weight |
| NEOSORB ® powder 60 (mp 96° C.) | 50 parts by weight |
| LYCASIN ® 80/55 with 80% of dry matter containing flavorings and dye perfumes | 25 parts by weight |

The base gum, previously heated to 75° C., was kneaded in a kneader of the KUSINER type provided with hot water circulation, in the presence of the liquid phase (LYCASIN ®+fragrances and dyes); the solid phase (NEOSORB ® powder) was added gradually in small amounts.

After dusting with mannitol, the paste was rolled and cut up into lozenges of conventional shape.

It was these lozenges that were coated.

To do this, 500 g of the abovesaid lozenges were placed in a laboratory dredger of the "LILLIPUT" type manufactured by FROGERAIS, equipped with an air blower to maintain the temperature of the bed of lozenges constant, and a thermometric probe located in this bed.

Rotary speed of the dredger: 25–30 rpm.

The coating product constituted by a sorbitol syrup was kept at constant temperature by means of a thermoregulated water-bath.

The coating syrup was added in successive batches (cycles) of 20 g of syrup, the introduction of these batches being done in some seconds every ten minutes, the time separating the end of one introduction from the following introduction being necessary to obtain the crystallization of the sorbitol and the evaporation of the water thus liberated.

The total amount of syrup to be added depends, in particular, on the thickness desired for the envelope.

The sorbitol used for the coating was constituted by a hydrogenated glucose syrup known by the name NEOSORB ® 70/02, whose purity on dry matter was 99%.

EXAMPLE 1

Two coating tests followed, the temperature of the bed in the course of coating being kept at 30° C., which value was necessitated by the softening of the gum.

The concentration of the coating syrup was 83% of dry matter.

The conditions and results of these tests are collected in Table I.

TABLE I

| Test No. | 1 | 2 |
|---|---|---|
| Concentration of coating syrup | 83% | 83% |
| Temperature of coating syrup | 70° C. | 40° C. |
| Temperature of the moving bed | 30° C. | 30° C. |
| Number of cycles | 5 | 5 |
| Weight of syrup applied | 100 g | 100 g |
| Observations | o | o |
| | o | o |

In this Table as well as in those which appear in the remainder of the description, the symbols shown in the line "Observations" characterised the results of the tests concerned. The significance of these symbols is indicated in the following Table:

| mediocre | very mediocre | poor | very poor | acceptable | average | good | very good |
|---|---|---|---|---|---|---|---|
| o | o | o | o | + | + | + | + |
| | o | o | o | | +. | + | + |
| | | o | o | | | + | + |
| | | | o | | | | + |

The surface of the coated products was swollen, there was poor distribution of the syrup and sticking occurred in the dredger after each addition.

The situation was, in fact, in both cases, under conditions of high supersaturation (saturation level: 1.70).

EXAMPLE 2

Five tests followed using a syrup with 70% of dry matter. The conditions and results are collected in Table II.

TABLE II

| Test no. | 3 | 4 | 5 | 6 | 7 |
|---|---|---|---|---|---|
| Syrup concentration | 70% | 70% | 70% | 70% | 70% |
| Syrup temperature | 90° C. | 70° C. | 65° C. | 40° C. | 40° C. |
| Temperature of the moving bed | 30° C. | 30° C. | 30° C. | 30° C. | 30° C. |
| Number of coating cycles | 14 | 21 | 21 | 15 | 21 |
| Total weight of syrup applied | 280 g | 420 g | 420 g | 300 g | 420 g |
| Observations | + | + | + | + | + |
| | | + | + | + | + |
| | | | | + | + |

It is noted that at 70% of dry matter, the improvement is very distinct. The saturation level is, for this concentration and at this temperature, 0.85.

There was still slight sticking at the time of each cycle, followed by a rapid fluidization of the moving mass.

The results improved progressively as the temperature of addition decreased. The good behavior on storage and the excellent momentary freshness on consuming the products obtained, is marked.

The conditions of these tests and the results recorded are collected in Table III.

TABLE III

| Test no. | 8 | 9 | 10 | 11 | 12 | 13 | 14 | 15 | 16 |
|---|---|---|---|---|---|---|---|---|---|
| Concentration of the syrup (%) | 70 | 70 | 70 | 70 | 70 | 70 | 70 | 70 | 70 |
| Temperature of the syrup (C.) | 90 | 70 | 60 | 90 | 70 | 90 | 80 | 70 | 40 |
| Number of cycles | 5 | 12 | 14 | 19 | 21 | 21 | 34 | 21 | 21 |
| Weight of syrup added (in g) | 100 | 240 | 280 | 380 | 420 | 420 | 680 | 420 | 420 |
| Temperature of the bed (C.) | 70 | 70 | 70 | 50 | 40 | 30 | 30 | 30 | 30 |
| Saturation level | <0.40 | <0.40 | <0.40 | 0.56 | 0.67 | 0.85 | 0.85 | 0.85 | 0.85 |
| Observations | o | o | o | o | + | + | + | + | + |
|  | o | o | o | o |  |  | + | + | + |
|  |  | o | o | o |  |  |  | + | + |
|  |  | o | o |  |  |  |  |  | + |

EXAMPLE 3

Procedure was as indicated in Example 2, the concentration of the syrup being at 75% of dry matter (saturation level : 1.08). The results recorded are very good, the temperature of the coating syrup not having exceeded 90° C. The good behavior on storage of the products obtained and their excellent immediate freshness was noted.

B. COATING OF THE COMPRESSION PRODUCTS

The cores to be coated were prepared on a rotary FROGERAIS compression machine with 16 punches of the MR2 type, operating by direct compression.

The product used was powdered sorbitol of the NEOSORB® 20/60 type flavored with mint and including 0.3% of lubricant constituted by magnesium stearate.

The coating was carried out by means of the equipment described with respect to the coating of the "sugarless" type chewing-gums.

In the case of the coating of these compression products with NEOSORB®, the temperature of the coating bed could be raised to 70° C., since the melting point of the NEOSORB® is higher than 95° C.

The additions of coating syrup were 20 g every 10 minutes.

It appears, on examination of the results gathered in this Table III, that, for a coating syrup with 70% of dry matter, it is advantageous to keep the temperature of the bed during coating below 40° C. Above this temperature, the solubility of sorbitol is very high and the syrup with 70% of dry matter, placed under these conditions, is in a state of very considerable under-saturation. At 30° C. (tests 13 to 16), a substantial improvement in the results is observed progressively as the temperature of the coating syrup increases, passing from 90° to 40° C.

For these tests, the good crystallinity of the layer, the excellent stability on storage and the good immediate freshness is marked.

EXAMPLE 5

Procedure was identical with that described with respect to Example 4, resorting to a syrup with a concentration of 75% of dry matter.

The results recorded on keeping the temperature of the moving bed of cores at 40° C. and, below 90° C., preferably below 70° C., the temperatures of the coating syrup, were excellent.

EXAMPLE 6

Eight tests followed in the manner indicated in Example 4, the concentration of the syrup being 80%.

The conditions and results are collected in the Table IV.

TABLE IV

| Test no. | 17 | 18 | 19 | 20 | 21 | 22 | 23 | 24 |
|---|---|---|---|---|---|---|---|---|
| Concentration of the syrup (%) | 80 | 80 | 80 | 80 | 80 | 80 | 80 | 80 |
| Temperature of the syrup (C.) | 70 | 110 | 80 | 70 | 60 | 110 | 50 | 70 |
| Number of cycles | 14 | 14 | 14 | 14 | 14 | 14 | 14 | 14 |
| Weight of the syrup added (in g) | 280 | 280 | 280 | 280 | 280 | 280 | 280 | 280 |
| Temperature of the bed (C.) | 70 | 50 | 50 | 50 | 50 | 45 | 45 | 30 |
| Saturation level | <0.50 | 0.80 | 0.80 | 0.80 | 0.80 | 0.95 | 0.95 | 1.43 |
| Observations | o | o | + | + | + | o | + | o |
|  | o | o |  | + | + | o |  | o |
|  | o |  |  |  |  |  |  |  |

EXAMPLE 4

By means of nine tests, the influence of temperature on the bed in the course of coating and of the temperature of a coating syrup, whose concentration was 70% of dry matter, was studied.

On reading these results, it is observed again that the temperature of the bed in the course of coating is a determining factor.

In test 17, the temperature existing in the bed, that is to say 70 C, was too high.

At a bed temperature of 50° C. the results were satisfactory when the temperature of the syrup was 80°, 70°, or 60° C. (tests 19, 20 and 21).

In the case of test 18, the temperature of the coating syrup being 110° C., the result was poor (there apparently occurs a partial refusion of the surface of the core at the moment of the addition of syrup, the sorbitol melting at 96° C.).

The result is satisfactory for test 23, the temperature of the bed being 45° C.

For test 22, the remarks are the same as for test 18.

In test 24, the temperature of the bed being 30° C., the coating syrup became too viscous at the moment of addition to the moving bed (saturation level : 1.43), whence a poor distribution of the liquid film.

C. COATING OF "BOILED SUGAR" BONBONS OF THE "SUGARLESS" TYPE.

Boiled sweets were prepared in the laboratory by evaporating to a residual moisture less than 0.5% a hydrogenated starch hydrolysate of the type marketed under the trademark LYCASIN ® 80/55.

The bonbons thus prepared were made into spherical form (diameter : about 1.5 cm.)

For the coating, the equipment and conditions of operation described above were used. The temperature of the moving bed was kept at a value below or at the most equal to 30° C.; this value was necessitated by the constituent material of the cores.

All the coatings were carried out on 500 g of cores.

The conditions and results are collected in the Table V

TABLE V

| Test no. | 25 | 26 | 27 | 28 |
|---|---|---|---|---|
| Concentration of the syrup (%) | 70 | 70 | 75 | 80 |
| Temperature of the syrup (C.) | 40 | 90 | 80 | 80 |
| Number of cycles | 15 | 15 | 15 | 15 |
| Temperature of the bed (C.) | 25 | 25 | 30 | 30 |
| Saturation level | 0,97 | 0,97 | 1,1 | 1,43 |
| Observations | + + + | + + + | + + | o o |

On examining the results collected in Table V, it is observed that, for a bed temperature of 25° to 30° C., the coating is good in the case of syrups having 70 and 75% of dry matter. The crystallinity of the surface is good, as is the immediate freshness (tests 25, 26, 27).

This coating improves the behavior under storage of the bonbons with LYCASIN ® and gives them a pleasant immediate freshness.

At 80% of dry matter (test 28), the coating syrup becomes viscous and considerable sticking occurs in the dredger, due to the superfusion of the liquid sorbitol.

As is self-evident and as emerges besides from the foregoing, the invention is in no way limited to those of its types of application and embodiments which have been more especially envisaged ; it encompasses, on the contrary, all modifications.

We claim:

1. Process for hard coating with sorbitol of cores of confectionery and pharmaceutical products, comprising:
    applying the sorbitol by addition, on a moving bed of cores to be coated, of a syrup having a concentration of dry matter comprised between 60 and 85% by weight and a richness in D-sorbitol higher than 80%,
    maintaining the temperature existing in the moving bed of cores to be coated at a value below 55° C.,
    selecting these conditions within the limits indicated in such a way that, when the sorbitol syrup arrives in contact with the cores to be coated, that is to say at the temperature maintained in the moving bed, the said sorbitol is at a saturation level comprised between 0.65 and 1.25.

2. Process according to claim 1, comprising applying a syrup of sorbitol having a concentration of dry matter comprised between 62 and 80% by weight.

3. Process according to claim 1, comprising maintaining the temperature in the moving bed of cores to be coated between 50° C. and 10° C.

4. Process according to claim 2, comprising maintaining the temperature in the moving bed of cores to be coated between 50° C. and 10° C.

5. Process according to claim 1, comprising selecting the conditions in such a way that the sorbitol is at a saturation level comprised between 0.8 and 1.15.

6. Process according to claim 2, comprising selecting the conditions in such a way that the sorbitol is at a saturation level comprised between 0.8 and 1.15.

7. Process according to claim 3, comprising selecting the conditions in such a way that the sorbitol is at a saturation level comprised between 0.8 and 1.15.

8. Process according to claim 4, comprising selecting the conditions in such a way that the sorbitol is at a saturation level comprised between 0.8 and 1.15.

9. Process according to claim 1, comprising, maintaining the temperature in the moving bed of cores to be coated between 40° and 15° C.

10. Process according to claim 2, comprising maintaining the temperature in the moving bed of cores to be coated between 40° and 15° C.

11. Process according to claim 3, comprising maintaining the temperature in the moving bed of cores to be coated between 40° and 15° C.

12. Process according to claim 4, comprising maintaining the temperature in the moving bed of cores to be coated between 40° and 15° C.

13. Process according to claim 5, comprising maintaining the temperature in the moving bed of cores to be coated between 40° and 15° C.

14. Process according to claim 6, comprising maintaining the temperature in the moving bed of cores to be coated between 40° and 15° C.

15. Process according to claim 7, comprising maintaining the temperature in the moving bed of cores to be coated between 40° and 15° C.

16. Process according to claim 8, comprising maintaining the temperature in the moving bed of cores to be coated between 40° and 15° C.

17. Process according to claim 1, comprising maintaining the temperature of the sorbitol syrup as applied below 100° C.

18. Process according to claim 1, comprising maintaining the temperature of the sorbitol syrup as applied below 90° C.

19. Process according to claim 1, comprising maintaining the temperature of the sorbitol syrup as applied below 70° C.

20. Process according to claim 1, comprising applying a syrup of sorbitol having a concentration of dry matter comprised between 65 and 77% by weight.

21. Process according to one of claims 1 to 20, comprising applying a syrup having a richness in D-sorbitol higher than 95%.

22. Process according to one of claims 1 to 20, comprising applying a syrup having a richness in D-sorbitol higher than 99%.

* * * * *